United States Patent [19]

Ladenson et al.

[11] Patent Number: 4,912,033
[45] Date of Patent: *Mar. 27, 1990

[54] CREATINE KINASE MB DETERMINATION METHOD

[75] Inventors: Jack H. Ladenson, University City; Hermant C. Vaidya, St. Louis; David N. Dietzler, St. Louis; Ann Y. Maynard, St. Louis, all of Mo.

[73] Assignee: Washington University, St. Louis, Mo.

[*] Notice: The portion of the term of this patent subsequent to Dec. 16, 2003 has been disclaimed.

[21] Appl. No.: 931,475

[22] Filed: Nov. 14, 1986

Related U.S. Application Data

[63] Continuation-in-part of Ser. No. 798,033, Nov. 14, 1985, abandoned.

[51] Int. Cl.$^4$ .............. G01N 33/573; G01N 33/577; C12N 5/00; A61K 39/395
[52] U.S. Cl. .................................... 435/7; 435/172.2; 435/240.27; 436/548; 530/387; 530/808; 530/809; 530/388; 935/103; 935/110
[58] Field of Search ............ 435/7, 17, 68, 172.2, 435/948, 240.27; 938/89, 106, 108, 110, 103; 436/501, 518, 548, 533, 534; 530/387, 808, 809, 388

[56] References Cited

U.S. PATENT DOCUMENTS

| | | | |
|---|---|---|---|
| 3,994,783 | 11/1976 | Rao et al. | 195/103.5 R |
| 4,237,044 | 12/1980 | Wurzburg et al. | 260/112 B |
| 4,260,678 | 4/1981 | Lepp et al. | 435/7 |
| 4,353,982 | 10/1982 | Gomez et al. | 435/7 |
| 4,387,160 | 6/1983 | Gomez et al. | 435/7 |

OTHER PUBLICATIONS

Sevier et al., Clin. Chem. 27(11):1797–1806, "Monoclonal Antibodies In Clinical Immunology" (1981).
Shell et al., Clinical Nuclear Cardiology, Greene & Stratton, New York, Ed. Barman, 462–478 (1981).
Jackson et al., Clin. Chem. 30, 1157–1162 (1984).
Sheehan et al., Clin. Chem. 31, 160–161 (1985).
Chan et al., Clin. Chem. 31, 465–469 (1985).
McBride et al., Clin. Chem. 31, 1099–1100 (1985).
Leykam et al., Clin. Chem. 29, 1219, Abst. 413-A (1983).
Vaidya et al., Biochim. Biophys. Acta. 790, 230–237 (1984).
Vaidya et al., Hybridoma 4(3), 271–276 (1985).
Vaidya et al., Clin. Chem. 32/4, pp. 657–663, (1986).

*Primary Examiner*—Esther M. Kepplinger
*Attorney, Agent, or Firm*—Irell & Manella

[57] ABSTRACT

A method of determining CK-MB isoenzyme in a biological fluid is disclosed which comprises subjecting a sample of said fluid to an assay system which includes incubating with monoclonal antibody specific to CK-MB isoenzyme, but not reactive with CK-MM or CK-BB. Methods for preparing antibodies with these characteristics and cell lines producing them are also disclosed.

19 Claims, 2 Drawing Sheets

CREATINE KINASE MB DETERMINATION METHOD

CROSS-REFERENCE TO RELATED APPLICATIONS

This is a continuation-in-part of U.S. Ser. No. 798,033, filed Nov. 14, 1985, now abandoned.

FIELD OF THE INVENTION

This invention relates to improved methods for the determination of creatine kinase MB isoenzyme in serum and other biological fluids, to antibodies useful in these methods, and to cell lines which produce these antibodies.

BACKGROUND ART

The enzyme creatine kinase (CK; EC 2. 7. 3. 2) catalyzes the reversible phosphorylation of creatine in which adenosine-5'-triphosphate (ATP) serves as the donor:

The forward reaction in which ATP is converted to adenosine-5'-diphosphate (ADP) is favored at about pH 9 whereas the reverse reaction is favored at about pH 7. The biological function of CK is the storage of high-energy creatine phosphate in the cell, and large quantities of the enzyme are present in skeletal muscle.

Chemically, CK is a dimer consisting of two molecular subunits designated as the M and B subunits which combine to give three isoenzymes: CK-BB, CK-MB and CK-MM. The three isoenzymes are located in the cytoplasm and each has a molecular weight of about 82,000 daltons. These isoenzymes can be separated by agarose gel electrophoresis in which the CK-BB isoenzyme migrates farthest toward the anode whereas the CK-MM isoenzyme migrates toward the cathode and the CK-MB isoenzyme migrates between the two.

The CK in the serum of the normal adult human consists mainly of the CK-MM isoenzyme with only trace quantities of the CK-MB. The CK-BB isoenzyme is not normally present in the serum at the detection limits of most CK assays. The detection of significant quantities of CK-MB in serum usually is indicative of acute myocardial infarction (AMI). However, CK-MB also has been found in the serum of patients with disorders other than AMI. Therefore, the CK-MB isoenzyme assay results need to be carefully interpreted by the medical profession. Nevertheless, most current assay methods are dedicated to the quantitation of CK-MB in AMI.

Various methods have been developed heretofore for the assay of CK, including spectrophotometric, colorimetric, fluorimetric, and coupled enzymatic methods.

In one typical coupled enzyme system, the reaction of creatine and ATP is initially catalyzed by CK to form creatine phosphate and ADP. This reaction is then coupled to two other enzyme reactions which employ phosphoenolpyruvate, reduced nicotinamide adenine dinucleotide (NADH) and the enzymes pyruvic kinase and lactate dehydrogenase. These reactions lead ultimately to the oxidation of NADH which is followed spectrophotometrically at 340 nm. This method was developed essentially by Tanzer and Gilvarg, *J Biol Chem* (1959) 234:3201–4, and modifications are described in U.S. Pat. No. 3,403,077.

Another coupled enzyme method is based on the reverse reaction in which creatine phosphate and ADP substrates react in the presence of CK to form creatine and ATP. The ATP generated serves in an auxiliary reaction to phosphorylate glucose in the presence of hexokinase (HK). The resulting glucose-6-phosphate (G-6-P) then becomes a substrate for the ultimate indicator reaction which is catalyzed by glucose-6-phosphate dehydrogenase (G-6-PDH) in the presence of nicotinamide adenine dinucleotide phosphate (NADP) to form 6-phosphogluconate and (NADPH). The production of NADPH is followed spectrophotometrically at 340 nm. This coupled enzyme system can be shown by the following series of equations:

(1)

(2)

(3)

The latter coupled enzyme system, first described by Nielsen and Ludvigsen and by Oliver, has been amplified by Rosalki, *J Lab Clin Med* (1967) 69:696–705, and further modifications are disclosed in U.S. Pat. Nos. 3,413,198; 3,485,724; 3,540,984; and 3,994,783.

Alternatively, the NADP and G-6-PDH in reaction 3, above, can be replaced with NAD and a G-6-PDH enzyme specific therefor, respectively, to produce NADH which can similarly be measured spectrophotometrically. The presence of NADH also can be detected by other means. Thus, the substrate solution can include a dye which is reducible by NADH, thereby permitting the use of colorimetric procedures.

In another alternate procedure, reactions 2 and 3, above, can be omitted and the creatine in reaction 1 can be reacted with α-napthol and diacetyl to form a pink-colored complex.

The most common assay procedures for CK-MB consist of measuring the enzymatic activity of CK-MB following separation from other CK isoenzymes on the basis of differences in charge utilizing electrophoresis or ion-exchange, or by immunoinhibition or a combination of immunoinhibition and immunoprecipitation. Alternatively, the mass of CK-MB has been measured by immunoassay either using one antibody for the assay of B subunits (CK-MB plus CK-BB) or two-site antibody techniques. In the two-site antibody techniques, one antibody, for instance to the B subunit, is attached to a solid phase to extract the isoenzymes containing that subunit and, after washing, a labeled (enzyme or $^{125}I$) antibody to the other, in this case M, subunit is added.

In a recently developed typical example of the solid phase two-site antibody technique for assay of CK-MB (such as the Enzygnost immunoassay manufactured by Cal Biochem-Boehring, La Jolla, California), serum is added to tubes that are coated with antibodies specific for the CK-B subunit so as to bind CK-MB, CK-BB, and macro-CK-1 (CK-BB associated with immunoglobulin). After a wash step that removes the CK-MM isoenzyme and all other enzymes that do not contain a CK-B subunit, a second antibody (which is specific for the CK-M subunit and labeled with horseradish peroxidase enzyme) is added, thereby labeling only the CK-MB that remains in the assay tube. The substrate, urea peroxide, is then added. The concentration of the generated color product is then related to the concentration of CK-MB in the sample.

The most recently described procedures for quantitatively measuring the amount of CK-MB in sera thus are those based on an immunologic approach. See, for example, U.S. Pat. Nos. 4,260,678; 4,353,982; and 4,387,160. Monoclonal antibodies (as distinguished from polyclonal antibodies) to the B and M subunits of CK also have been developed for such assays and are described, for example, by Wurzburg and Strobel, *J Clin Chem Clin Biochem* (1981) 19:543–544; Morris and Head, FEBS Lett (1982) 145:163–168; Morris and Head, *Biochem J* (1983) 213:417–425; Jackson et al, Ibid (1983) 215:505–512. Assays for CK-MB using such antibodies have been further evaluated and reported by Jackson et al, *Clin Chem* (1984) 30:1157–1162; Sheehan and Haythorn, Ibid (1985) 31:160–161; Chan et al, Ibid (1985) 31:465–469; McBride et al, Ibid (1985) 31:1099–1100.

The prior assays have varying degrees of sensitivity to the other two isoenzymes of CK, namely CK-MM and CK-BB. In addition, interference by adenylate kinase (when CK activity is measured), by macro-CK-1 (CK associated with immunoglobulin) and by macro-CK-2 (mitochondrial CK) also have been encountered. Also, interference due to non-specific binding is a frequent problem in two-site assays (Boscato, L. M. et al., *Clin Chem* (1986) 32:1491–1495).

DISCLOSURE OF THE INVENTION

The invention provides improved methods and materials for the determination of CK-MB isoenzyme in serum and other biological fluids. These methods employ a monoclonal antibody or derivatives thereof that recognize only CK-MB and not the other isoenzymes. Use of this antibody permits the direct specific measurement of the isoenzyme in serum and other biological fluids by its enzymatic activity in a solid phase assay. Thus, this class of antibody, one member of which is designated Conan-MB, is utilized to extract CK-MB isoenzymes from serum and other biological fluids. The CK-MB in the biological sample can then be determined by exposing the adsorbed CK-MB isoenzyme to a CK reagent system and measuring the catalytic activity, or can be detected by other means. For example, the enzyme activity in catalyzing the ATP/ADP conversion can be determined by monitoring the absorbance change at 340 nm due to NADH or NADPH, or the reaction can be linked to another known reaction which can be followed spectrophotometrically. In representative examples, the assay using the Conan-MB monoclonal antibody coated onto latex particles employs this approach. This protocol showed no interferences and gave excellent agreement with a commercially available solid phase two-site enzyme immunoassay. Other protocols in which MB-specific antibody is useful can, of course, also be employed.

Thus, in one aspect, the invention is directed to MB-specific monoclonal antibody preparations useful in determining CK-MB in appropriate samples. In another aspect, the invention is directed to cell lines, especially hybridomas, which are capable of producing the MB-specific monoclonal antibody preparations. In still other aspects, the invention is directed to methods to prepare such cell lines and monoclonal antibodies, and to methods for assay of CK-MB in biological and other samples using the monoclonal antibody preparations of the invention.

A particular embodiment of the MB-specific monoclonal antibody preparations is designated Conan-MB, and the hybridoma cell line which produces the Conan-MB monoclonal antibody is on deposit at the American Type Culture Collection, Rockville, Maryland, under accession number ATCC HB 8939.

BRIEF DESCRIPTION OF THE DRAWINGS

FIG. 3 is a graphical representation which shows the influence of CK-MM, CK-BB, mitochondrial CK and hemolysis on the direct assay of CK-MB in one embodiment of the invention. The control CK-MB value was 62 U/l of purified human CK-MB. The hemolysate was prepared by freezing washed human red cells stored less than 24 hours. Purified CK-MM, CK-BB and mitochondrial CK were utilized. The values in the presence of the higher amounts of isoenzymes are corrected for a small residual activity present after two washes of the latex beads. This residual activity was determined by using control beads for the assay and was 35.9 U/l for the 200,000 U/l of CK-MM and 25.0 U/l for the 250,000 U/l of CK-BB.

MODES OF CARRYING OUT THE INVENTION

A. Definitions

As used herein "immunologically reactive with" refers to typical antibody-antigen reactions which are mediated by the specificity of the variable region of immunoglobulins to specific epitopes.

"Immunologically reactive derivative" of an antibody refers to portions of the antibody which retain the ability to recognize the epitopes ordinarily recognized by the antibody from which they are derived. Such derivatives commonly include, for example, Fab, Fab', and F(ab')$_2$ fragments of immunoglobulins. Preparation of such immunologically reactive derivatives is well understood in the art, and often confers advantages when the antibodies are to be used in vivo, or when the functional effects of the total immunoglobulin molecule are not desired.

"Cross-reactive with" in describing the characteristics of an immunoglobulin or its derivatives refers to the ability to recognize the same epitope as the referenced antibody or derivative. This ability can be recognized by assessing the ability of the cross-reacting material to block the immunological reaction of the referenced immunoglobulin.

As used herein, one unit (U) of activity is defined as equal to one micromole of ATP formed per minute at 37° C.

"Cell line" refers to an immortalized cell, cell culture, multiplicity of identical cells, and the progeny thereof. It is recognized that the progeny, and some of the members of the "identical" collection may not be absolutely identical to the original cell from which the line is derived, but may differ in genetic makeup due to chance mutations. These mutated progeny are, however, included within the definition as long as the essential characteristics of the cell line are maintained. In terms of the present invention, a cell or its progeny falls within the definition so long as the ability to secrete antibodies of the required characteristics—i.e., specificity for the CK-MB isoenzyme—is retained.

"Specific for CK-MB isoenzyme" refers to the ability of an antibody or derivative to react immunologically with CK-MB, to the exclusion of CK-BB or CK-MM.

The term "Conan-MB" refers specifically to the antibody secreted by ATCC HB-8939 and to this particular cell line. Thus, "Conan-MB" is used to designate both the cell line and its product. The term "Conan-type MB" refers to antibodies which compete with Conan-MB in reaction with CK-MB and to the cell lines secreting them. The term "MB-specific antibodies" refers to any monoclonal antibody which is specific for CK-MB, whether it recognizes the same epitope as Conan-MB or not.

Thus, there are three levels of similarity with the antibodies secreted by the deposited cell line. The antibodies secreted by the deposited cell line per se, Conan-MB, cross-react with "Conan-type MB" monoclonal antibodies since both compete for the same or similar epitope. The general class of MB-specific monoclonal antibody preparations react with CK-MB to the exclusion of CK-BB or CK-MM, and these latter isoenzymes do not compete with CK-MB for immunoreactions with MB-specific monoclonal antibodies; however, not all members of the general class MB-specific monoclonal antibodies compete with or cross-react with Conan-MB. Some may recognize different epitopes on the CK-MB isoenzyme than does Conan-MB itself, although the epitopes are unique to CK-MB as opposed to CK-BB or CK-MM.

"CK reagent", as used herein, refers to a collection of components which can be used to measure the enzymatic activity of the creatine kinase. Creatine kinase is enzymatically active in all three of its isoenzymic forms and catalyzes the interconversion of creatine phosphate-and-ADP with creatine-and-ATP, as set forth above. The reagent will thus contain the appropriate reactants for the conduct of this reaction, plus reagents to produce a detectable result from the products.

For example, in Example 2, the "CK reagent" is a commercially available reagent mixture containing AMP, ADP, creatine phosphate, NAD, yeast HK, and G-6-PDH and various buffering and stabilizing components. This mixture is marketed by Electro-Nucleonics, Inc. under the name Gemini CK$_{LTS}$ reagent.

In Example 3, the "CK reagent" is a 30:1 mixture of a "substrate" solution containing 20.92 g/l Bis-Tris, 1.010 g/l ADP, 2.14 g/l Mg(oAc)$_2$, 3.60 g/l D-glucose, 2.00 g/l NAD, 1.85 g/l AMP, 0.95 g/l EGTA, 2500 U/l HK and 1650 U/l G-6-PDH, and a "kicker" solution containing 2.092 g/l Bis-Tris and 332.8 g/l creatine phosphate.

B. Production of MB-Specific Antibodies

In general, the MB-specific antibodies can be prepared by a specific protocol which involves immunization of an appropriate mammalian subject with purified CK-MB, obtaining anti-MB secreting cells from the peripheral blood lymphocytes or spleen of the immunized animal at a time when the antibody titers in the serum are high, immortalizing these antibody secreting cells, and then screening the immortalized cells for production of the desired antibodies. The screening procedure is of the utmost importance, and includes immunoreactions with purified CK-MB and verifying a lack of cross-reactivity of the antibodies with purified CK-BB and CK-MM.

It is important to the success of the preparation of MB-specific antibody secreting cell lines to use a purified CK-MB isoenzyme as the immunogen in the initial immunization. The enzyme may be purified from human skeletal and heart muscle as described by Leykam, Dietzler, and Ladenson, *Clin Chem* (1983) 29:1219 (Abstract 413-A), and by Vaidya, Dietzler, Leykam, and Ladenson, *Biochim Biophys Acta* (1984) 790:230-237, incorporated herein by reference. This purification procedure employs tissue homogenization, ammonium sulfate fractionation, ion-exchange chromatography such as with DEAE-Sepharose, followed by affinity chromatography or chromatofocusing. Variations on this disclosed method are also workable.

For example, in affinity chromatography, a substance is specifically and reversibly adsorbed by a complementary binding substance (ligand) immobilized on an insoluble support (matrix). A variety of matrices and ligands may be used. Preferred affinity chromatography materials are Affi-Gel ® Blue, which is an agarose with reactive blue dye commercially available from Bio-Rad, Richmond, Calif., and 5'-AMP-Sepharose ® which is formed by coupling N$^6$(6-aminohexyl-) 5'-AMP to Sepharose (agarose) and commercially available from Pharmacia Fine Chemicals AB, Uppsala, Sweden.

A particularly preferred method for purification of CK-MB is made possible by the availability of the Conan-MB secreted by the hybridoma ATCC HB-8939 or other MB-specific antibodies of the invention. Because these antibodies are so exquisitely specific for the desired isoenzyme, they make suitable ligands for affinity chromatography in procedures to purify this material. The antibody can be conjugated to any suitable matrix, including Sepharose, latex, agarose, or polyacrylamide. Means for immobilizing antibodies to solid supports are, of course, numerous and well understood in the art.

In the chromatofocusing procedure, proteins are eluted as sharply focused, well separated zones in a linear pH gradient according to their isoelectric point. The proteins, after initially binding at the top of the column to a Polybuffer Exchange resin, migrate down as the pH gradient develops. The rate of movement to a particular level in the pH gradient down the column is lower than the rate of flow of the Polybuffer. Trailing proteins are carried downward and catch up with the region where they bind to the column and, thereby, maintain a narrow zone width. Further background information on chromatofocusing can be had by reference to the manufacturer's bulletin: *Chromatofocusing with Polybuffer ® and PBE ®*, Pharmacia Fine Chemicals, Uppsala, Sweden, 1982; Richey and Beadling, *Amer Lab* 13, October 1981, pp. 100–102; and Sluyterman, *Trends in Biochem Sci* (1982) 7:168–170.

The purified CK-MB isoenzyme is then used as an immunogen to produce cells capable of secreting MB-specific antibodies. Mice (or other suitable mammalian subjects) are immunized by injection with the purified CK-MB isoenzyme until a high titer of antibody is detectable in the serum. A well-immunized subject thus identified is preferably injected with additional CK-MB. After a suitable period of time, the spleen cells or peripheral blood lymphocytes, preferably spleen cells, are harvested and immortalized.

A preferred mouse strain for use in the immunization is the A/J strain such as is available from Jackson Laboratories, Bar Harbor, Maine. This is a well-known mouse strain having genetic characteristics as defined in *Biological Handbooks III: Inbred and Genetically Defined Strains of Laboratory Animals*, Part 1, Mouse and Rat, Compiled and Edited by Altman and Katz, FASEB, Bethesda, Maryland, 1979, at page 21, incorporated herein by reference. For further information on the A/J strain, see also Bangham, *Mouse News Lett* (1965) 33:68; Dickie, Ibid (1966) 34:30; and *Handbook of Genetically Standardized JAX Mice*, Heiniger and Dorey, eds, The Jackson Laboratory, Bar Harbor, Maine, 3d Ed., 1980, especially Section 2, pp. 1–32.

Immortalization can be effected by fusion with a myeloma as originally described by Kohler and Milstein, *Nature* (1975) 256:495–497; *Eur J Immunol* (1976) 6:511–519. According to this method, tissue-culture adapted mouse myeloma cells are fused to spleen cells from immunized mice to obtain the hybrid cells that produce large amounts of single antibody molecule. Of course, other immortalization procedures known in the art, such as infection with Epstein-Barr virus, or transfection with viral DNA, can also be used.

For the Kohler and Milstein procedure, a preferred mouse myeloma cell line is the Sp2/0-Ag14 cell line. This is a well-known cell line of BALB/c origin defined by Schulman, Wilde and Kohler, *Nature* (1978) 276:269–270. These cells, which do not synthesize immunoglobulin (Ig) chains, are available from the Basel Institute for Immunology, Basel, Switzerland, and the American Type Culture Collection, Rockville, Maryland, under accession number ATCC CRL-1581.

A preferred method of carrying out the fusion of the myeloma cells and the spleen cells is by the general procedure described by Galfre et al, *Nature* (1977) 266:550–552, in which polyethylene glycol (PEG), for example, PEG 1500, is used as the fusing agent for the cells growing in monolayers. Immortalized cells can be selected by culturing in HAT (hypoxanthine, aminopterin and thymidine) selection medium as described, for example, by Littlefield, *Science* (1964) 145:709. The choice of selection medium, of course, depends on the nature of the immortalization process. If immortalization is through fusion, the fusion partner, such as the myeloma, confers immortality on the antibody-secreting line and must have deficiency characteristics which are complemented by the antibody-secreting partner in the context of the selection medium.

The immortalized cells must then be screened for those which secrete antibody of the correct specificity.

A critically important part of the process for preparation of the MB-specific antibodies herein is, indeed, the choice of an appropriate screening procedure which will result in identification of immortalized cells secreting antibody of the correct specificity.

The supernatants from the immortalized cells first are screened for secretion of antibodies which bind CK-MB. This can be done using conventional immunoassay procedures such as immunoassay.

Conventional general RIA procedures were originally described, for example, by Yalow et al, *J Clin Invest* 39, 1157 (1960); and solid phase RIA was first developed by Catt and Tregear, *Science* 158, 1570–1572 (1967). In general, since polyvinyl surfaces will tightly adsorb nanogram amounts of most proteins, an immobilized second antibody (antisera) is used to capture primary antibody which in turn can bind radiolabeled antigen in a competition-type assay. In one illustration, the RIA can be performed by applying the supernatants to multiwell microtiter plates which have been coated, for example, with anti-mouse antibody, and then detecting bound antibody using labeled, purified CK-MB.

The group of hybridomas or other cells thus identified as secreting antibodies capable of binding CK-MB is then screened for those which do not bind to CK-MM or CK-BB. This can be done in a variety of protocols, but the most straightforward and preferred method is a competition assay using purified monoclonal antibodies from the supernatants. The purified preparations are applied to microtiter wells coated with anti-mouse IgG and the wells are treated with labeled CK-MB in the presence of varying amounts of competing CK-BB or CK-MM. Those cell lines producing antibodies which continue to bind CK-MB and thus resist competition by either CK-MM or CK-BB are then selected.

The foregoing protocol may be employed either on the original culture supernatants, or may utilize partially purified culture medium or ascites fluid after amplification of those cultures which are shown to secrete antibody reactive with CK-MB. Based on the experience disclosed herein, the majority of the CK-MB reactive antibodies prepared by the illustrated method are specific for this isoenzyme and do not react with CK-MM and CK-BB; thus, little is wasted by the amplification procedure, as might be the case if the majority of the immortalized cell lines did not produce antibodies of the desired specificity. A useful confirmatory test for the specificity to the desired isoenzyme is more conveniently performed on partially purified antibodies from such amplified supernates or ascites fluids. In this procedure, the antibodies produced are labeled using, for example, $^{125}$I or other suitable label and contacted with electrophoresis gels containing bands corresponding to the separated isoenzymes. Preparations wherein the immunoglobulins bind exclusively to the separated isoenzyme CK-MB, but not to the bands corresponding to CK-BB or CK-MM, are then selected.

In the illustrated procedure below, of 13 hybridomas obtained which secreted antibodies against CK-MB, eight produced antibodies which were specific to this isoenzyme.

To amplify the antibody production, the immortalized cells are cultured in vitro in culture medium, or, in the alternative, are injected into mice in which they produce ascites tumors that permit growth of the cells and generation of large amounts of monoclonal antibody.

Following production, the monoclonal antibody can be isolated and purified from the tissue culture medium or ascites fluid by various known methods such as ammonium sulfate precipitation, dialysis, affinity chromatography, ion exchange chromatography, ultrafiltration, adsorption with polyelectrolyte copolymers, and the like methods of protein separations. Preferred methods employ affinity chromatography on protein A-agarose columns, for example, protein A-Sepharose ®, followed by dialysis or ultrafiltration. Protein A is a polypeptide (mol. wt. 42,000) isolated from *Staphylococcus aureus* which binds Ig molecules without interacting at the antigen binding site. Protein A-Sepharose ® is commercially available from Pharmacia Fine Chemicals AB, Uppsala, Sweden.

These and other such suitable methods for isolation and purification of monoclonal antibodies are described in general by Goding, *Monoclonal Antibodies: Principles and Practice*, Academic Press, London and New York, 1983, and U.S. Pat. No. 4,533,496.

C. Affinity Chromatography

The CK-MB-specific monoclonal antibodies prepared as described above are useful for affinity purification of CK-MB from biological fluids or culture media. The use of such antibodies in these purification procedures employs affinity chromatography techniques which are generally understood. In a typical approach, the monoclonals or their immunologically reactive fragments are conjugated to a solid support, such as agarose, polyacrylamide, or latex through standard linking technology, such as through use of bifunctional linking agents or by direct binding. The mixture from which the CK-MB purification is desired is then passed through a column or filter containing the supported antibody preparation using conditions under which an immunological reaction occurs between the antibody and the CK-MB. The CK-MB is then eluted by imposing conditions which dissociate the antigen-antibody complex selectively. Such conditions include alteration of pH, alteration of temperature, and control of ionic strength.

D. Assay For CK-MB

The CK-MB-specific antibodies of the invention are particularly useful as components of an assay for the presence, absence, or amount of CK-MB in biological or other samples, including, for example, assay in serum as an indicator of myocardial infarction. Protocols for assays utilizing this antibody vary widely, and may employ direct measurement of CK-MB retrieved using this antibody or may employ competitive or sandwich assay techniques.

Suitable exemplary protocols include the following.

In one particularly useful set of protocols, competitive immunoassays in which labeled CK-MB competes with the CK-MB contained in the sample for immobilized CK-MB-specific antibodies can be used. In this assay type, the CK-MB-specific antibodies, bound to solid support, such as microtiter wells, beads, or to a column, are placed in contact with the sample to which has been added varying amounts of labeled CK-MB. The higher the concentration of CK-MB in the sample, the less labeled CK-MB is allowed to bind to the solid support. The amount of label diagnostic for the sample CK-MB can be measured either in the solution remaining after treatment with the support, or may be measured on the support itself or eluted from the support. If the label is measured as that remaining in solution, the amount of label measured is directly proportional to the CK-MB content of the sample; the reverse is true if the label bound to the support is used as a measure. The label may be any of those commonly known and employed in such assays, including, without limitation, radioactive isotopes, fluorescent compounds, chromogenic compounds, or enzymes which catalyze reactions producing detectable results.

In an alternative type of protocol, a sandwich assay may be used in which the MB-specific monoclonal antibody of the invention is used to extract the CK-MB in the sample, which is then detected by use of labeled anti-CK-M or anti-CK-B—e.g., antibodies which are specific to either subunit (or, indeed, polyclonal antisera or other monoclonals reactive with CK-MB). This assay may be conducted on a solid phase support or an immunoprecipitate may be formed initially which is then separated and labeled. The protocol may, of course, be reversed and the anti-CK-M or anti-CK-B be used as the capture immunoglobulin and labeled MB-specific antibodies used to detect the immunoprecipitate or adsorbate.

Antibodies specific for the M or B subunits of CK may be used as either polyclonal or monoclonal preparations. They are available commercially, or can be prepared using standard methods similar to those described above, which are described in the art for Igs of these particular specificities.

In addition to the foregoing, a direct immunoassay may be performed by incubating the sample to be tested with the MB-specific antibodies of the invention wherein the antibodies or their fragments have been immobilized on solid particles such as, for example, carrier beads, or on solid surfaces. The beads or other inert solids are then washed and the CK-MB activity bound to the antibody is measured after incubation with a specific CK reagent such as the components of a coupled enzyme reaction system. In such protocols, initial incubation can be carried out at room temperature, whereas the incubation with the CK reagent is often carried out at about 37° C.

In these protocols, which rely on CK activity, it is desirable to take precautions to prevent denaturation. Since CK enzymes are known to be relatively unstable in blood serum samples, the addition of a small but activating amount of a sulfhydryl (thiol) compound such as, for example, β-mercaptoethanol, cysteine, glutathione or dithiothreitol can be added to the assay reaction medium. See, for example, U.S. Pat. Nos. 3,403,077 and 3,540,984, for use of such additives.

The inert carrier particles can be, for example, glass, silica, agarose, dextran, polystyrene, polyvinylchloride, styrene/divinylbenzene copolymer and other such organic or inorganic materials which can be fabricated in the form of spherical beads, although nonspherical surfaces also can be used. In addition magnetized beads can be used to aid separation. The beads can be of submicron particle size or larger, for example, up to about a centimeter in diameter. The non-spherical surface can be a glass or plastic tube surface, or a microtiter well.

In one illustration below, latex beads are used, and can be polystyrene latex beads of a particle size less than about one micron in diameter. Such beads have been commonly used as carrier particles in antigen/antibody reactions such as described, for example, by Singer and Plotz, *Amer J Med* (1956) 21:888–892 and U.S. Pat. No. 3,088,875.

There are a number of alternative chemistries available. In one illustrated embodiment, CK reagent is a buffered aqueous solution containing effective amounts of creatine phosphate, ADP, glucose, HK, G-6-PDH and NAD, pH about 7.

The CK reagent components for this embodiment and the latex beads or other inert carrier particles are well-known materials and are also available commercially. Thus, the ADP and NAD+ compounds can be obtained from mammalian muscle tissue and are generally available commercially as water soluble salts, usually as the sodium salts. Creatine phosphate also is available from mammalian muscle tissue while glucose is generally obtained commercially by the hydrolysis of cornstarch. The HK and G-6-PDH enzymes can be obtained from yeasts and other microorganisms as seen, for example, from U.S. Pat. No. 3,794,562. The HK enzyme has an absolute cofactor requirement for $Mg^{+2}$ ion for activity and this can be supplied by the addition of a small but effective amount of a water-soluble magnesium salt, for example, magnesium sulfate or magnesium acetate, to the reaction medium. The formation of NADH in this system can be detected spectrophotometrically at 340 nanometers or by fluorescence. In addition, the NADH formed can be used to reduce dyes such as iodonitrotetrazolium violet (INT) via an electron carrier, such as diaphorase, to produce colored compounds which can be detected spectrophotometrically in the visible range.

Other enzyme systems which generate NADH or NADPH may also be substituted.

In addition, coupled enzyme systems or other means to detect specifically one or more of the products of the CK catalyzed reaction in the direction chosen can be substituted for the CK reagent illustrated. For example, materials which form specific colored complexes with creatine or creatine phosphate, or which further react with ATP in any way, may also be used.

In one particular alternative, the ATP generated in the creatine kinase reaction may be detected using a luciferase system. This enzyme, extracted from fireflies and commercially available, catalyzes the conversion of luciferin in the presence of oxygen to products which are of sufficiently lower energy that light is emitted in the course of the reaction. This bioluminescence can be used as a direct method for detecting CK-MB quantitatively or qualitatively.

The following detailed examples will further illustrate the invention although it will be understood that the invention is not limited to them. Parts are by weight unless otherwise specified.

EXAMPLE 1

Production and Characterization of Monoclonal Antibodies

Preliminary tests showed that immunized A/J mice had much higher antibody titers to CK-MB in their serum than did conventionally used BALB/c mice.

The illustrative procedures were conducted as follows:

A. Immunization Protocol

Eight-week old female A/J mice, $H-2^a$ haplotype, (Jackson Laboratories, Bar Harbor, MA 04609), were injected intraperitoneally with 25 $\mu$g of human creatine kinase-MB emulsified in an equal volume of complete Freund's adjuvant (Sigma Chemical Co., St. Louis, MO 63178). Four weeks and eight weeks later, the same amount of antigen in incomplete Freund's adjuvant (Sigma Chemical Co.) and phosphate buffered saline (PBS, 50 mmol/l sodium phosphate, pH 7.2, containing 150 mmol/l NaCl) was similarly administered. A final boost of 25 $\mu$g antigen in PBS was given four days before fusion at least three weeks after the third injection.

The CK-MB isoenzyme used in this immunization was isolated from human heart muscle and purified by a combination of ion exchange chromatography and affinity chromatography. Thus, the heart tissue was extracted with a buffer comprising 50 mmol Tris, pH 7.3, containing 100 mmol/l EDTA, 10 mmol/l 2-mercaptoethanol (Buffer A). A 40–70% $(NH_4)_2SO_4$ cut of the tissue extract was dialyzed and then subjected to DEAE-Sepharose ion exchange column chromatography using a 0–325 mmol/l NaCl linear gradient in Buffer A. The CK-MB peak was detected by agarose gel electrophoresis. The CK-MB fractions were then subjected to Affi-Gel Blue affinity column chromatography to remove albumin using a 0–250 mmol/l NaCl gradient in Buffer A to elute the CK-MB. Contaminant LDH was removed by subjecting the CK-MB to 5'-AMP-Sepharose affinity column chromatography which binds NAD+-dependent dehydrogenases and ATP-dependent kinases. The purified CK-MB was collected in the flow through, concentrated, dialyzed and stored at −70° C. in 50% glycerol.

B. Fusion Technique

Spleens were removed aseptically from the immunized mice. Splenocytes ($10^8$) were fused with Sp2/0-Ag14 cells ($10^7$), a BALB/c myeloma cell line, in the presence of polyethylene glycol (PEG 1500) essentially following the published procedure of Kohler and Milstein, *Nature* 256, 495–497 (1975).

C. Screening

Screening of the hybridomas producing antibodies against CK-MB was carried out by using solid phase radioimmunoassay. Goat anti-mouse IgG (H+L) antibodies (Pel-Freeze® Biologicals, Rogers, AR 72756) (2 mg/l in 100 mmol/l sodium borate, pH 8.5, containing 150 mmol/l NaCl) were coated onto 96 well round bottomed microtiter plates (Dynatech, Alexandria, VA 22314) by incubating 100 $\mu$l of goat anti-mouse IgG overnight at 4° C. for 2 hours at 37° C. The plates were washed with Tween®-saline (0.5 ml Tween-20, 8.77 g NaCl, 0.02 g $NaN_3$ per liter). This was followed by addition of 100 $\mu$l of hybridoma supernate followed by incubation and washing as above. The antibodies present in the supernates against human CK-MB were detected by adding 100,000 cpm of radiolabeled antigen (CK-MB, purified as above) per well and incubating overnight at 4° C. The radiolabeled CK-MB was diluted in PBS containing 10 g/l bovine serum albumin and 1 mmol/l 2-mercaptoethanol. The plates were washed, dried and the bound, radiolabeled CK-MB was counted on a Packard $\gamma$ counter. The results were considered positive if the counts bound to the well were at least twofold above the negative control wells containing unrelated hybridoma supernates. For positive controls, wells were developed using appropriately diluted anti CK-M subunit and anti CK-B subunit specific monoclonal antibodies obtained from Hybritech (San Diego, CA 92121). Hybridomas producing antibodies to CK-MB were cloned in soft agar and stored under liquid nitrogen in Dulbecco's modified Eagle's medium (DMEM) with 10% dimethyl sulfoxide and 30% horse serum.

D. Purification of Monoclonal Antibody From Ascites

Pristane primed CAF$_1$/J mice (Jackson Laboratories) were injected intraperitoneally with $10^6$ hybrid cells and ascites fluid was collected 1-2 weeks later. Ascites fluid produced by each cell line were pooled and stored at $-20°$ C. after removal of the cell debris by centrifugation. Monoclonal antibody from the ascites fluid was purified using a protein A affinity column system (MAPS ™, Bio-Rad, Richmond, CA 94804). The antibody peak eluted from the column was concentrated using an Amicon YM-50 ultrafiltration cell having a mol. wt. cutoff of 50,000 Daltons and then dialyzed against PBS and stored at $-70°$ C. The purity of the monoclonal antibodies was checked by electrophoresis on agarose gel.

E. Agarose Gel Electrophoresis

Electrophoresis of ascites fluid was performed using agarose gel (Corning agarose film No. 470100, American Scientific Products, Palo Alto, CA 94306) and barbitol Buffer (PHAB, Corning No. 470180). Electrophoresis was carried out for 40 minutes at 90 V. Electrophoretic separation of CK isoenzymes was similarly performed for 30 minutes using Corning Agarose film (No. 470104) and Mopso buffer: 3-(N-Morpholino)-2-hydroxypropane sulfonic acid (Corning No. 470046). For staining the proteins, gels were fixed and stained in a mixture of methanol, acetic acid and water (40:10:50) containing 0.125% Coomassie blue. The background was destained in the same mixture without Coomassie blue before air drying.

F. Determination of Isotype

Isotype determination of the monoclonal antibody was performed by the Ouchterlony radial immunodiffusion technique. (See Ouchterlony, *Handbook of Immunodiffusion and Immunoelectrophoresis*, Ann Arbor Sc. Publ., 1968). Double immunodiffusion discs and mouse isotype specific antisera were obtained from Miles Scientific, Naperville, IL 60566.

G. Determination of Specificity

The specificity of the monoclonal antibodies was determined by competitive radioimmunoassay. This assay was similar to the RIA used for screening hybridoma supernatant except that the binding of radiolabeled CK-MB to the monoclonal antibodies was competed with various concentrations of purified CK isoenzymes. 100 μl of affinity purified monoclonal antibody (2 mg/l in PBS containing 10 g/l bovine serum albumin) was bound to the goat anti-mouse IgG immobilized on the microtiter plate. A 100 μl mixture of labeled CK-MB (100,000 cpm) and 0-1000 ng of competing isoenzyme of CK, (CK-BB or CK-MM) was then added and incubated overnight at 4° C. The plates were then washed and dried, and bound radiolabeled CK-MB was counted on a Packard γ-counter.

The specificity of Conan-MB was confirmed by allowing radiolabeled antibody to bind to CK isoenzymes separated on agarose gel by electrophoresis. Following electrophoresis, gels were fixed in a mixture of isopropanol, acetic acid and water (25:10:65) for 30 min., washed twice with deionized water for the same time and incubated in 50 ml of PBS containing 10 g/l bovine serum albumin (BSA) and 500,000 cpm of $^{125}$I-labeled antibody for 4 hours at room temperature. Unbound radioactivity was washed off with PBS. Gels were then dried, exposed to XAR-5 X-ray film (Eastman Kodak Company, Rochester, NY 14650) for 24 hours at $-70°$ C. with an intensifier screen and developed in an automatic film processing unit.

Results

The above procedures produced the following results.

Monoclonal antibody characterization

Fusion of the spleen cells of four immunized A/J mice with BALB/c myeloma cell line SP2/0-Ag14 generated 13 hybridomas secreting antibodies against human CK-MB. By the competitive RIA, it was found that eight of the 13 hybridomas produced antibodies specific for human CK-MB which did not recognize human CK-MM or CK-BB. In addition, four hybridomas producing antibodies specific to the B subunit and one producing antibody specific to the M subunit were found.

Ascites fluid produced by injection of one of the cloned hybridomas producing antibody specific to CK-MB (Conan-MB) was characterized by immunodiffusion to be of the IgG-2b subclass with kappa light chains.

Figure 1:
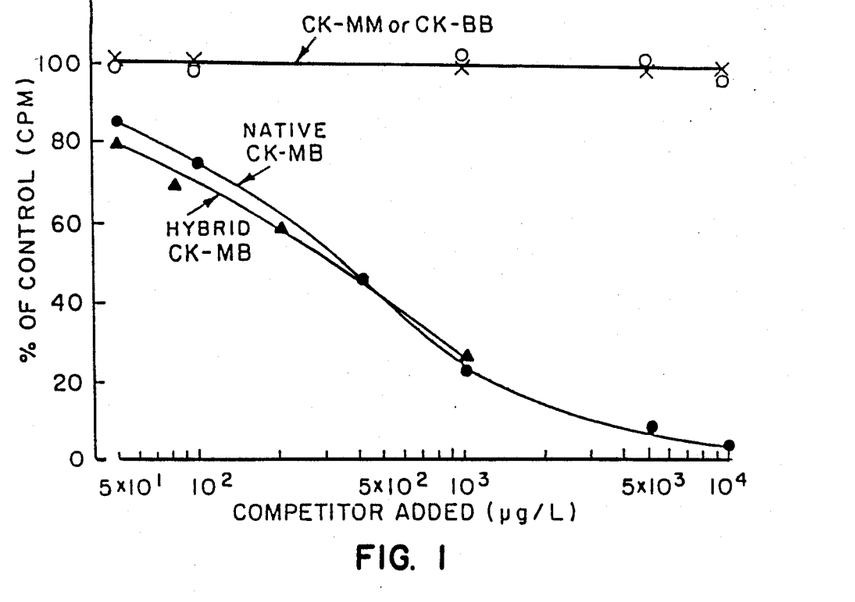
FIG. 1 is a graphical representation which shows the specificity of Conan-MB monoclonal antibody as determined by competitive RIA. Immobilized monoclonal antibody Conan-MB was exposed to various concentrations of CK-MM (X), CK-BB (O), native CK-MB (●), and hybrid CK-MB (■) along with 100,000 cpm of $^{125}$I CK-MB. The counts of $^{125}$I CK-MB bound to Conan-MB as a percentage of the counts bound with no competitor present are plotted against the logarithm of competitor added (μg/l).

Competitive RIA demonstrating the specificity of Conan-MB is shown in FIG. 1. Conan-MB did not recognize CK-MM or CK-BB even at concentrations up to 10 mg/l. The specificity of Conan-MB was confirmed by using hybrid CK-MB which gave an identical inhibition pattern as the native CK-MB purified from human heart. Moreover, radiolabeled Conan-MB bound to CK-MB but not to CK-MM or CK-BB separated by agarose gel electrophoresis.

Further characterization revealed that binding of Conan-MB to CK-MB did not appear to influence the enzyme activity. Such was also the case when CK-MB was extracted from the solution by Conan-MB immobilized on latex beads. Because of the specificity and ability to extract enzymatically active CK-MB, Conan-MB was used in a clinical assay for the direct measurement of CK-MB activity.

EXAMPLE 2

Determination of CK-MB

Clinical Samples and Standards

Serum samples submitted to the Barnes Hospital Chemistry Laboratory or the Coronary Care Unit Laboratory for CK-MB analysis were stored at 4° C. after stabilization to a final concentration of 10 mmol/l 2-mercaptoethanol and assayed within 5 days. Samples were assayed by the direct CK-MB procedure of this invention and also, for comparison, by a commercially available two-site enzyme immunoassay (Enzygnost CK-MB, Behring Diagnostics, La Jolla, CA 92037).

A heat-inactivated serum pool (56° C. for 30 min) was prepared from excess sera obtained from the chemistry laboratory and stored at $-70°$ C. The heat treatment was sufficient to inactivate creatine kinase activity and allowed the seum pool to be used as a matrix for CK-MB standards and dilution of samples with high CK-MB activity. CK-MB used as standard was purified as described hereinbefore. The enzyme activity of the high standard was determined with a Flexigem ™ centrifugal analyzer at 37° C. using modification of the procedure of Rosalki, *J Lab Clin Med* 69, 696–705 (1967), in which creatine phosphate served as the substrate and hexokinase and glucose-6-phosphate dehydrogenase were the coupling enzymes (Electronucleonics Inc., Fairfield, NJ 07006). Calibrator 4 (matrix of BSA) from the Enzygnost CK-MB assay (Behring Diagnostics) and serum pools of low and high CK-MB activity were used as controls. All other reagents were purchased from Sigma Chemical Co., St. Louis, MO 63178.

Immobilization of antibody on Latex beads

Monoclonal antibody was immobilized by passive adsorption onto 0.8 micron diameter polystyrene latex beads (LB-8, Sigma Chemical Co.). The beads were diluted 20-fold to a 5 g/l suspension in coating buffer (0.1 mol/l sodium phosphate, pH 6.0) and pelleted in an Eppendorf microfuge (15,000×g, 5 min). The beads were resuspended to 5 g/l in coating buffer containing 0.1 g/l monoclonal antibody and incubated overnight at 4° C. with gentle rotation. The coated beads were pelleted, washed twice with Tris Buffered Saline (TBS) (20 mmol/l Tris, pH 7.2, 150 mmol/l NaCl) and resuspended to 5 g/l in TBS. The amount of mouse immunoglobulin left in the supernatant was determined by a sandwich enzyme immunoassay. The amount of monoclonal antibody bound to the latex beads was determined by subtracting the concentration of monoclonal antibody left in the supernatant from that in the coating solution. More than 90% of the antibody was bound to the beads under these conditions so that 10 μl of coated bead suspension contained approximately 1.0 μg monoclonal antibody.

Direct Assay Procedure for CK-MB

The assay for CK-MB consisted of two incubations separated by a washing step. During the initial extraction or immunoadsorption phase, serum CK-MB was bound to monoclonal antibody immobilized on latex beads. The adsorbed enzyme was then exposed to CK reagent in the enzymatic phase. The resulting absorbance was measured at 340 nm and was proportional to enzyme activity.

The assay was performed as follows:

(1) Pipette 100 μl serum samples, standard solutions or controls into 1.5 ml polypropylene Eppendorf microfuge tubes. Standards were prepared by diluting purified CK-MB to an activity of ~125 U/l. Dilutions of this solution were made to provide standards ranging from 4–128 U/l. The enzymatic activity of the high standard was measured kinetically and the activity of the other standards calculated using the appropriate dilution factor. Add 100 μl heat-inactivated serum pool to standard and non-serum-containing control tubes. Bring volume to 1 ml with Assay Buffer (TBS+1 mmol/l 2-mercaptoethanol).

(2) Add 25 μl of monoclonal antibody-coated latex particles which contain approximately 2.5 μg of monoclonal antibody. Incubate for 30 min. at room temperature.

(3) Chill tubes in a 4° C. water bath and pellet beads in Eppendorf microfuge (15,000×g, 5 min.) Wash the beads twice with 1 ml Assay Buffer.

(4) Resuspend beads in 0.25 ml Assay Buffer. Add 0.50 ml CK-reagent. Transfer the tubes to a 37° C. water bath for 30 min.

(5) Pellet beads, remove 0.5 ml of supernatant and read $A_{340}$. Calculate U/l of CK-MB by comparison with the slope of the least squares regression $A_{340}$ and activity of the standards.

Absorbance readings were performed with the Flexigem™ centrifugal analyzer. Samples with values >100 U/l were reassayed after 2- and 4-fold dilution in heat-inactivated serum.

Assay method

Figure 2:
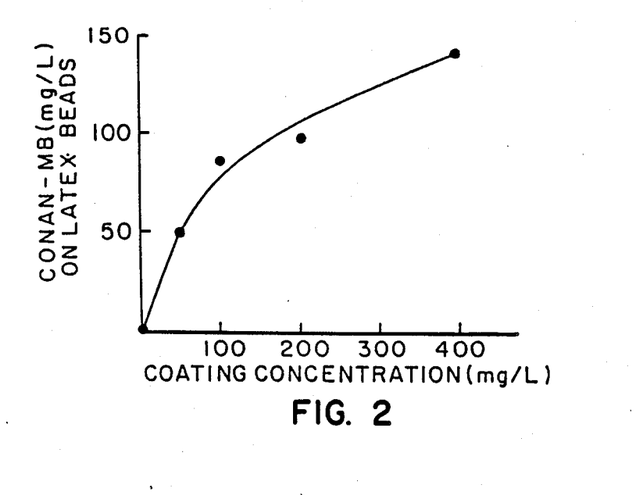
FIG. 2 is a graphical representation which shows the coating of latex beads with monoclonal antibody Conan-MB in one embodiment of the invention. Conan-MB immobilized on 0.8 micron latex beads (5 g/l) after overnight incubation at 4° C. is plotted against increasing concentrations of antibody.

The assay is performed in two steps and each was optimized with regard to serum concentration, time and temperature. Latex particles (0.8 micron) were selected for the solid phase because of the high coating density achievable and their ready availability. At the concentration used for coating (0.1 g/l) greater than 95% of Conan-MB adsorbs to the beads in a 5 g/l suspension. At lower concentrations, virtually 100% of Conan-MB adsorbs but the final coated concentration is less. At higher coating concentration, a greater percentage of antibody is not bound suggesting saturation of the protein binding sites on the beads. See FIG. 2.

The optimum amount of immobilized Conan-MB was determined by adding increasing amounts of a 5 g/l suspension of coated beads to four doses of CK-MB in PBS containing 10 g/l BSA representing enzyme activity from 32–256 U/l. After an overnight incubation at 4° C., the Conan-MB coated beads were pelleted and washed. The enzyme activity adsorbed on the beads was measured as $A_{340}$ after 30 min. of incubation with CK reagent at 37° C. and the enzyme activity left in the supernatants was measured by kinetic CK assay also at 37° C. The amount of enzyme activity on the beads increases with increasing amount of immobilized Conan-MB until a plateau is approached at 2 μg Conan-MB. Greater than 90% of CK-MB could be bound at each activity of enzyme tested. Similar conclusions were reached by examining the enzyme activity remaining in the supernatant. It is preferred to use 2.5 μg Conan-MB in the assay.

When CK-MB was added to normal serum, a smaller percentage of enzyme activity was adsorbed by immobilized Conan-MB after overnight incubation at 4° C. This effect occurred even at high doses of antibody (up to 16 μg) but appeared to be minimized by increasing dilution of serum. Therefore, it is preferred to dilute 100 μl serum to a volume of 1000 μl with Assay Buffer. Standards and controls were mixed with 100 μl heat-inactivated serum and then diluted to 1000 μl with Assay Buffer. These conditions allow approximately 70% of CK-MB in standards to bind at all doses tested. The recovery of CK-MB was assessed by adding 10.2 U/l or 77.9 U/l to a serum sample initially assayed to be 21.7 U/l. The recovery was 106.9% and 94.1% respectively.

The effects of temperature and time on the immunoadsorption step also were assessed. The activity of CK-MB was constant for 24 hours at either room temperature or 4° C. as determined in the supernatants from incubation with control beads (coated with mouse IgG). At 37° C. the activity decreased progressively after 30 min. of incubation with the control beads. CK-MB activity was maximally bound to the Conan-MB coated beads after 30 min. at room temperature or 2 hours at 4° C. After these times there was a small decrease in bound CK-MB at 4° C. but a progressive decrease at room temperature. These changes were associated with proportional increases in the CK-MB in the supernatants, thereby suggesting dissociation of the CK-MB from the monoclonal antibody or dissociation of the CK-MB-antibody complex from the latex beads. It is preferred to incubate samples with Conan-MB coated beads for 30 min. at room temperature followed by immediate chilling in an ice-water bath to minimize release of CK-MB during the subsequent washing steps.

After washing and resuspension of the beads at 4° C., the second step of the assay is initiated by the addition of CK-reagent and transfer of the tubes to a 37° C. water bath. The volume and time of incubation was set to produce $A_{340}$ of 1.3 for the high standard ($\sim$125 U/l) and $A_{340}$ of 0.16 for a standard containing 15 U/l CK-MB which is the expected upper reference limit for normal subjects. The increase in $A_{340}$ was linear for concentrations of standards tested over the 30 min. incubation. The conditions of the second step can be altered to increase or decrease the sensitivity of the assay.

A small amount (1 mmol/l) of 2-mercaptoethanol was added to the assay mixture to enhance enzymatic activity and maintain stability. The addition of 10 mmol/l also enhances the activity but appears to increase the dissociation of captured enzyme from immobilized Conan-MB.

Figure 3:
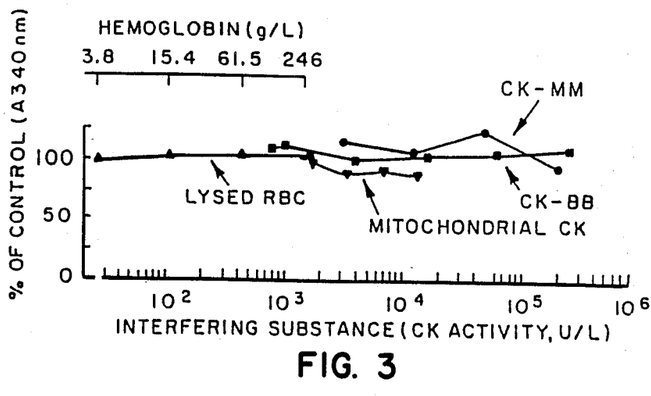

The influence of potential interfering substances was assessed. With the preferred assay conditions, it was found that serum did not influence the results even when present up to 80% of the initial assay volume. These results, performed with a 30 min. incubation at room temperature, were at odds with those found with an overnight incubation at 4° C. (see above). Heat-inactivated serum was used as a matrix for dilutions and standards since the apparent dissociation of CK-MB from the latex beads was greater when serum was present than when only buffer was present. The addition of lysed red blood cells as a source of adenylate kinase did not influence the results even when the hemoglobin (as an assessment of hemolysis) was as high as 246 g/l. See FIG. 3. The addition of up to 200,000 U/l of CK-MM or 250,000 U/l CK-BB caused only a non-specific effect. With such high amounts of added enzyme there was a residual enzymatic activity which was not removed by the two washes of the latex beads. When the assay was performed with control beads and the small residual enzyme activity, e.g., 36 U/l for the 200,000 U/l CK-MM, was deducted no influence of CK-BB or CK-MM was found. See FIG. 3. These results were confirmed by repeating the interference studies utilizing four washes of the latex beads. No influence due to mitochondrial CK was found.

The within assay (n=10) CV was determined twice and found to be 5.3% and 9.5% for a low serum pool (13.0 U/l); and determined twice and found to be 3.2% and 1.2% for a high serum pool (105.1 U/l). The between assay CV was 13.2% for the calibrator 4 (12.8 U/l) (11 different days); 18.7% for the low serum pool (11 assays) and 4.5% for the high serum pool (11 assays).

Figure 4:
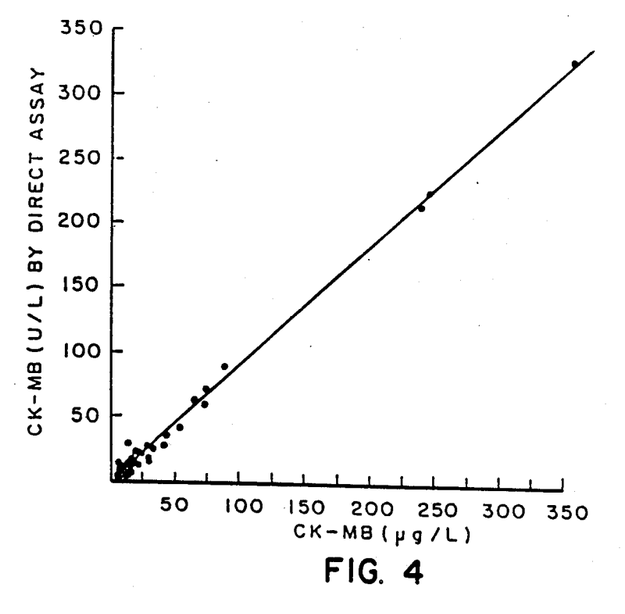
FIG. 4 is a graphical representation which shows the comparison of CK-MB activity (U/l) determined by direct assay in one embodiment of the invention and CK-MB concentration determined by a commercially available two-site immunoassay (μg/l). Fifty samples were measured by both assays. The linear regression was Y=0.915 X+0.35 with a correlation coefficient of 0.997.

The results with the direct assay for CK-MB according to the present invention were compared with the two-site immunoassay used by the Barnes Hospital clinical laboratories. See FIG. 4. The correlation was 0.997 and the slope 0.915, thereby indicating comparability of results.

EXAMPLE 3

Direct Assay on Macrobeads

A direct assay similar to that set forth in Example 2 above can also be conducted on macrobeads of approximately 0.25 inch diameter. The assay is performed as follows:

Mutiwell reaction trays such as those available from Abbott Laboratories are used for the assay, and 10/µl of 0.2M β-mercaptoethanol is pipetted into each well. 100 µl samples of standards or test materials are used, with dilutions being performed, if required, in heat-inactivated serum pool (HISP). HISP is prepared by heating excess serum for 30 min at 56° C., and then storing the incubated serum at −70° C. in 50 ml aliquots. Standards are prepared using serial dilutions from the highest concentration standard (S4), which is 10 µl stock CK-MB (about 62,000 U/l) in 5 ml HISP and checking the activity kinetically of Flexigem ™, as described in Example 2. A standard curve is prepared using dilutions of this standard (S4), wherein for a determined value of S4 at 108 U/l, S3 contains 36 U/l, S2 contains 12 U/l, and S1 contains 4 U/l. S0 is blank. The standard solutions are stable for 1 week when stored at 4° C. or for at least 3 months when stored at −70° C.

One Conan-MB bead is then added to each well. The beads are prepared as described in Example 2 except that in place of latex microbeads, ¼ inch polystyrene beads with specular finish are used. The beads are rinsed before addition to the wells in 50 mM Tris, pH 7.5.

The wells are then incubated 1 hour at room temperature on a platform shaker at about 150 rpm and then washed on an automated washer such as the Proquantum ® (Abbott Laboratories) using 10 ml water per well. Each bead is then transferred to a separate tube to which is added 300 µl CK reagent which is similar to that of Example 2 but without the addition of sulfhydryl activator such as 2-mercaptoethanol.

The tubes containing the individual beads are incubated at 37° C. for 45 minutes before stopping the reaction by the addition of 1 ml color-stopping reagent which contains 100 mM Tris, pH 7.5, 5 mM 1,2-Diaminocyclohexane-N,N,N',N'-tetra acetic acid (DCTA), 0.1 mg/ml R-iodonitrotetrazolium violet (INT), and 1 U/ml diaphorase. These reagents are commercially available and were purchased from Sigma Chemical Co.

After stopping the reaction, the tubes are removed from the water bath and the absorbance read at 492 nm after 5 minutes.

The results showed good correlation with CK-MB concentration as determined by the two-site immunoassay used by the Barnes Hospital Clinical Laboratories. The correlation was 0.978 and the slope 0.800 when comparing 639 samples thus indicating comparability of results.

Various other examples will be apparent to the person skilled in the art after reading the present disclosure without departing from the spirit and scope of the invention. It is intended that all such other examples be included within the scope of the appended claims.

We claim:

1. A composition comprising monoclonal antibody or immunologically reactive derivative thereof which antibody or derivative is immunologically reactive with CK-MB isoenzyme but not with CK-MM or CK-BB isoenzymes.

2. The composition of claim 1 wherein the antibody or derivative is cross-reactive with Conan-MB, ATCC HB 8939.

3. The composition of claim 1 wherein the antibody or derivative is Conan-MB, ATCC HB 8939 or derivative thereof.

4. The composition of claim 1 wherein the antibody or derivative is of the IgG-2b subclass with k light chains.

5. The composition of claim 1 wherein the monoclonal antibody is produced by a hybridoma generated by fusing mouse myeloma cells with spleen cells from a mouse immunized with CK-MB isoenzyme.

6. A cell line which produces an antibody immunologically reactive with CK-MB isoenzyme but not with CK-MM or CK-BB isoenzymes.

7. The cell line of claim 6 wherein said antibody is cross-reactive with Conan-MB, ATCC HB 8939.

8. The cell line of claim 6 which is a hybridoma.

9. The hybridoma cell line of claim 8 which is ATCC HB 8939 (Conan-MB).

10. A method to determine CK-MB isoenzyme in a sample, which method comprises:
   contacting said sample with a composition of claim 1 to effect an immunoreaction between CK-MB in the sample and the antibody and derivative thereof in the composition,
   separating the immunoreacted components from the remainder of the sample, and
   detecting the amount of immunoreaction between any CK-MB isoenzyme in the sample and the antibody or derivative thereof in the composition.

11. The method of claim 10 wherein the antibody or derivative thereof is conjugated to a solid phase support.

12. The method of claim 10 which further includes detecting the amount of immunoreaction by measuring the catalytic activity of CK-MB.

13. The method of claim 10 which further includes detecting the amount of immunoreaction by immunoreaction with an additional antibody.

14. The method of claim 10 which comprises incubating the sample with a solid-phase support to which is bound antibody or derivative thereof;
   removing the support from contact with the sample; and
   measuring the amount of CK-MB bound to the support with a CK-reagent.

15. The method of claim 14 in which the CK reagent is a CK-coupled enzyme reagent system.

16. The method of claim 15 in which the CK-coupled enzyme reagent comprises a buffered aqueous mixture of creatine phosphate, ADP, glucose, HK, G-6-PDH, and NAD at about pH 7.

17. The method of claim 14 in which the solid phase is provided by latex beads.

18. The method of claim 17 in which the latex beads are polystyrene latex beads of less than about one micron in diameter.

19. The method of claim 17 in which the solid phase is provided by macroscopic polystyrene beads.

* * * * *

UNITED STATES PATENT AND TRADEMARK OFFICE
CERTIFICATE OF CORRECTION

PATENT NO. : 4,912,033
DATED : Mar. 27, 1990
INVENTOR(S) : Jack H. Ladenson; Hermant C. Vaidya; David N. Dietzler; Ann Y. Maynard It is certified that error appears in the above-identified patent and that said Letters Patent is hereby corrected as shown below:

Title page:
  Item [45] Date of Patent: please delete "*".

Please delete " [*] Notice: The portion of the term of this patent subsequent to Dec. 16, 2003 has been disclaimed."

Signed and Sealed this

Second Day of March, 1993

Attest:

STEPHEN G. KUNIN

*Attesting Officer*  *Acting Commissioner of Patents and Trademarks*

UNITED STATES PATENT AND TRADEMARK OFFICE
CERTIFICATE OF CORRECTION

PATENT NO. : 4,912,033
DATED : 27 March 1990
INVENTOR(S) : Jack H. Ladenson, Hermant C. Vaidya, David N. Dietzler, Ann Y. Maynard It is certified that error appears in the above-indentified patent and that said Letters Patent is hereby corrected as shown below:

Column 19,
Claim 10, line 5, delete "and" (second occurrence) and insert --or--.

Signed and Sealed this

Twentieth Day of September, 1994

Attest:

BRUCE LEHMAN

*Attesting Officer*  *Commissioner of Patents and Trademarks*